United States Patent
Wang et al.

(10) Patent No.: US 12,127,789 B2
(45) Date of Patent: Oct. 29, 2024

(54) SUBTLE CORNEA DEFORMATION IDENTIFICATION METHOD AND DEVICE BASED ON PIXEL-LEVEL CORNEAL BIOMECHANICAL PARAMETER

(71) Applicants: TIANJIN EYE HOSPITAL, Tianjin (CN); WENZHOU UNIVERSITY OF TECHNOLOGY, Wenzhou (CN)

(72) Inventors: Yan Wang, Tianjin (CN); Xuan Chen, Tianjin (CN); Zuoping Tan, Tianjin (CN); Riwei Wang, Tianjin (CN)

(73) Assignees: TIANJIN EYE HOSPITAL, Tianjin (CN); WENZHOU UNIVERSITY OF TECHNOLOGY, Wenzhou (CN)

( * ) Notice: Subject to any disclaimer, the term of this patent is extended or adjusted under 35 U.S.C. 154(b) by 0 days.

(21) Appl. No.: 18/202,725

(22) Filed: May 26, 2023

(65) Prior Publication Data
US 2024/0172938 A1   May 30, 2024

(30) Foreign Application Priority Data
May 26, 2022   (CN) .......................... 202210581366.7

(51) Int. Cl.
*A61B 3/10*   (2006.01)
*A61B 3/00*   (2006.01)
(Continued)

(52) U.S. Cl.
CPC ............ *A61B 3/107* (2013.01); *A61B 3/0025* (2013.01); *A61B 3/145* (2013.01)

(58) Field of Classification Search
CPC ..... A61B 3/1005; A61B 3/102; A61B 3/1025; A61B 3/113; A61B 3/1015; A61B 3/0083;
(Continued)

(56) References Cited

U.S. PATENT DOCUMENTS

2014/0114145 A1\*   4/2014   Wang ................... A61B 3/165
                                                                600/301

FOREIGN PATENT DOCUMENTS

| CN | 108346472 A | * | 7/2018 | |
| CN | 114387545 A | * | 4/2022 | |
| WO | WO-2017223341 A1 | * | 12/2017 | ............. A61B 3/102 |

OTHER PUBLICATIONS

Xuchun, Wang; "Risk Prediction Study on Liver Cirrhosis Complicated with Hepatic Encephalopathy Based on Resampling and Ensemble Learning Algorithm"; Medical and Health Science and Technology Series of China Master's Theses Full-text Database; E064-190; Jan. 15, 2022; 91 pages.

\* cited by examiner

*Primary Examiner* — Dawayne Pinkney
(74) *Attorney, Agent, or Firm* — Thorpe North & Western, LLP; David W. Osborne

(57) ABSTRACT

The present disclosure relates to a subtle cornea deformation identification method and device based on a pixel-level corneal biomechanical parameter, including the following steps: step 1, sampling and analyzing a dynamic video of corneal stress deformation in a historical database, and calculating pixel-level data; and step 2, configuring an ensemble classifier based on a sampling result and detecting a local change in corneal biomechanics, thus identifying a subtle cornea deformation. The present disclosure has high measurement accuracy and is capable of detecting a local subtle biomechanical change.

5 Claims, 2 Drawing Sheets

(51) Int. Cl.
  *A61B 3/02* (2006.01)
  *A61B 3/107* (2006.01)
  *A61B 3/14* (2006.01)
(58) Field of Classification Search
  CPC ........... A61B 3/1225; A61B 3/02; A61B 3/16;
       A61B 3/005; A61B 3/107
  USPC ....... 351/212, 205, 206, 209, 210, 218, 221,
       351/222, 245, 246; 600/398–406
  See application file for complete search history.

SUBTLE CORNEA DEFORMATION IDENTIFICATION METHOD AND DEVICE BASED ON PIXEL-LEVEL CORNEAL BIOMECHANICAL PARAMETER

CROSS REFERENCE TO RELATED APPLICATION

This patent application claims the benefit and priority of Chinese Patent Application No. 202210581366.7, filed with the China National Intellectual Property Administration on May 26, 2022, the disclosure of which is incorporated by reference herein in its entirety as part of the present application.

TECHNICAL FIELD

The present disclosure belongs to the technical field of subtle cornea deformation identification, and relates to a subtle cornea deformation identification method and device, and in particular, to a subtle cornea deformation identification method and device based on a pixel-level corneal biomechanical parameter.

BACKGROUND

Currently, there are two major devices to measure corneal biomechanics, namely, ocular response analyzer (ORA) and corneal visualization scheimpflug technology (Corvis ST).

ORA is used to flatten cornea dynamically and bidirectionally by air pulse, record the bidirectional applanation timepoint with optoelectronic signals, and to measure the applanation pressures P1 and P2 for two times, thus obtaining corneal hysteresis (CH) and a corneal resistance factor (CRF) capable of reflecting corneal biomechanics.

Corvis ST is used to produce two applanation statuses under the action of jet pulse by scanning at a rate of 4330 frame/s within a horizontal extent of 8 mm and to capture 140 images within 31 ms using ultra-high-speed Scheimpflug computed tomography, thus obtaining the corneal dynamic response parameters, oscillogram and dynamic corneal deformation videos to characterize corneal biomechanics.

However, there exist the following defects in the above methods: the existing commercial device serve to obtain the biomechanical parameters that reflect the overall mechanical information of the cornea, and due to insufficient measurement accuracy, it is very difficult to measure a local subtle mechanical change.

No disclosed patent literatures the same as or similar to the present disclosure have been found after searching.

SUMMARY

The objective of the present disclosure is to overcome the shortcomings of the prior art and to provide a subtle cornea deformation identification method and device based on a pixel-level corneal biomechanical parameter. The present disclosure has high measurement accuracy and is capable of detecting a local subtle mechanical change.

The present disclosure adopts the following technical solution to resolve the technical problem:

a subtle cornea deformation identification method based on a pixel-level corneal biomechanical parameter is provided, including the following steps:

step 1, sampling and analyzing a dynamic video of corneal stress deformation in a historical database, and calculating pixel-level data; and step 2, configuring an ensemble classifier based on a sampling result and detecting a local change in corneal biomechanics, thus identifying a subtle cornea deformation.

Further, the step 1 is specifically as follows: capturing and partitioning the dynamic video of corneal stress deformation in a historical database, extracting a corneal contour in each position according to a pixel, fitting a curvilinear equation of the corneal contour, and calculating the pixel-level data based on pixel point.

Further, the pixel-level data includes: variation of full contour length at first applanation, variation of full contour length at second applanation, maximum depression area, time at the first applanation, time at the second applanation, maximum curvature, depth of a thinnest point at the first applanation, depth of a thinnest point at the second applanation, depth of a thinnest point at maximum depression, length at the first applanation, length at the second applanation, peak distance, relative displacement of a thinnest point (1 mm), and relative displacement of a thinnest point (2 mm).

Further, the step 2 specifically includes:
(1) configuring a base classifier based on T sampling sets containing m training samples obtained by the sampling as follows:

where a predicted label of x from an i-th base classifier is assumed as $$h_i(x) \in \{-1, +1\}$$

and the x has a real label of $$y = f(x) \in \{-1, +1\}$$

the base classifier has an error rate of E, namely, directed to each base classifier $h_i$, there exists $$P(h_i(x) \neq f(x)) = \epsilon$$

T base classifiers are combined by a voting method, and when more than half of the base classifiers predict +1, ensemble classification gains +1, namely, when there are more than half base classifiers that predict 1, then $$\sum_{i=1}^{T} h_i(x) > 0$$

when there are more than half base classifiers that predict −1, then $$\sum_{i=1}^{T} h_i(x) < 0$$

and finally, the ensemble classifier has a result:

$$F(x) = \text{sgn}(H(x)) = \text{sgn}\left(\sum_{i=1}^{T} h_i(x)\right)$$

when the error rate of the base classifier is assumed independent, an ensemble classifier error rate is:

$$P(F(x) \ne f(x)) = \sum_{k=0}^{\lfloor T/2 \rfloor} \binom{T}{k}(1-\epsilon)^k \epsilon^{T-k}$$

that is, the error rate of the base classifier reduces exponentially as a number T of the base classifiers increases constantly; according to an inequation Hoeffding, when δ>0, k=(p−δ)n;

$$P(H(n) \le (p-\delta) \le e^{-2\delta^2 n}$$

when the ensemble classifier error rate is substituted into the inequation Hoeffding, and when $\delta>0, k=(p-\delta)n \Rightarrow \lfloor T/2 \rfloor = (1-\epsilon-\delta)T$ $$P(H(T) \le (1-\epsilon-\delta)T) \le e^{-2\delta^2 T}$$

δ is settled according to a condition $\lfloor T/2 \rfloor = (1-\epsilon-\delta)T$ and substituted into the inequation above to solve an error rate of the ensemble classifier;

$$P(H(T) \le \lfloor T/2 \rfloor) \le e^{-2\delta^2 T} \le e^{-2(1-\epsilon-\frac{1}{2})^2 T} = e^{-\frac{T}{2}(1-2\epsilon)^2}$$

(2) inputting the pixel-level corneal biomechanical parameter in the step 1 to each of the sampling sets, training a base learner, and integrating the base learners to obtain an ensemble learning model, and inputting a sample to be measured into the ensemble classifier, to obtain a sample category; and (3) calculating sample categories of all the samples to be measured, and determining a local change result of corneal biomechanics;

further, the sample category in the step (2) is obtained specifically by:

using a category with a maximum number of votes as the sample category by a voting method, and when two categories gain an equal number of votes, randomly choosing one of the two categories as a final category of the sample.

Further, the determining a local change result of corneal biomechanics in the step (3) specifically includes:

(i) regarding one category and all other categories except for the one category as a dichotomous data model to calculate a true positive rate (TPR) and a false positive rate (FPR), and defining the FPR and the TPR as an x axis and a y axis, respectively to obtain a visual receiver operating characteristic (ROC) curve;

where TPR denotes a capability to distinguish correctness from all positive samples, and FPR denotes a capability to distinguish an error from all negative samples;

(ii) calculating a precision, a recall rate and an F1 Score to evaluate a performance of a tripartite model;

where the precision represents a proportion of correctly predicted quantities in predicted classification, and is equal to TP/(TP+FP);

the recall rate denotes a proportion of correctly predicted quantities in true classification, and is equal to TP/(TP+FN);

the F1 score denotes a harmonic mean of the precision and the recall rate; 1/F1 Score-½ (1/precision+1/recall rate);

where, T: predicted correct actually; F: predicted mistaken actually; P: predicted positive; N: predicted negative; TP: determined as a positive accuracy; FP: false positive rate, namely, a negative is determined as a positive; and FN: false negative rate, namely, a positive is determined as a negative.

A subtle cornea deformation identification device based on a pixel-level corneal biomechanical parameter includes:

a pixel-level data computation module, configured to conduct sampling analysis on a dynamic video of corneal stress deformation in a historical database, and to calculate pixel-level data; and a subtle cornea deformation identification module, configured to configure an ensemble classifier based on a sampling result, and detect a local change in corneal biomechanics, thus identifying a subtle cornea deformation.

The present disclosure has the following advantages and beneficial effects:

1. The present disclosure provides a subtle cornea deformation identification method and device based on a pixel-level corneal biomechanical parameter, which is different from the prior art, namely, a rough change in overall biomechanics is evaluated by acquiring overall information of cornea, and the change emerges only when there exists more obvious change on the whole. The present disclosure serves to calculate 14 pixel-level corneal biomechanical parameter to accurately evaluate a local subtle biomechanical change by analyzing a video of corneal stress deformation in a historical database based on the theory that the weaker the biomechanics is, the more serious the corneal deformation produced is, thereby identifying a subtle corneal deformation. Therefore, the present disclosure has higher prediction accuracy and good consistency.

2. The present disclosure serves to extract a corneal contour in each position and to calculate new pixel-level biomechanical parameter by analyzing the dynamic video of corneal stress deformation in a historical database, which may measure a local subtle biomechanical change; the present disclosure is different from the prior art which reflects the information of the whole cornea via biomechanical parameters.

3. An ensemble classifier is adopted herein; machine learning algorithm is sometimes called a "black box" and thus, may help avoid a selection bias and improve the measurement on the change of biomechanical characteristics. Therefore, accuracy may be improved by evaluating some machine learning algorithms on a same dataset and choosing an optimal algorithm.

DETAILED DESCRIPTION OF THE EMBODIMENTS

Figure 1:
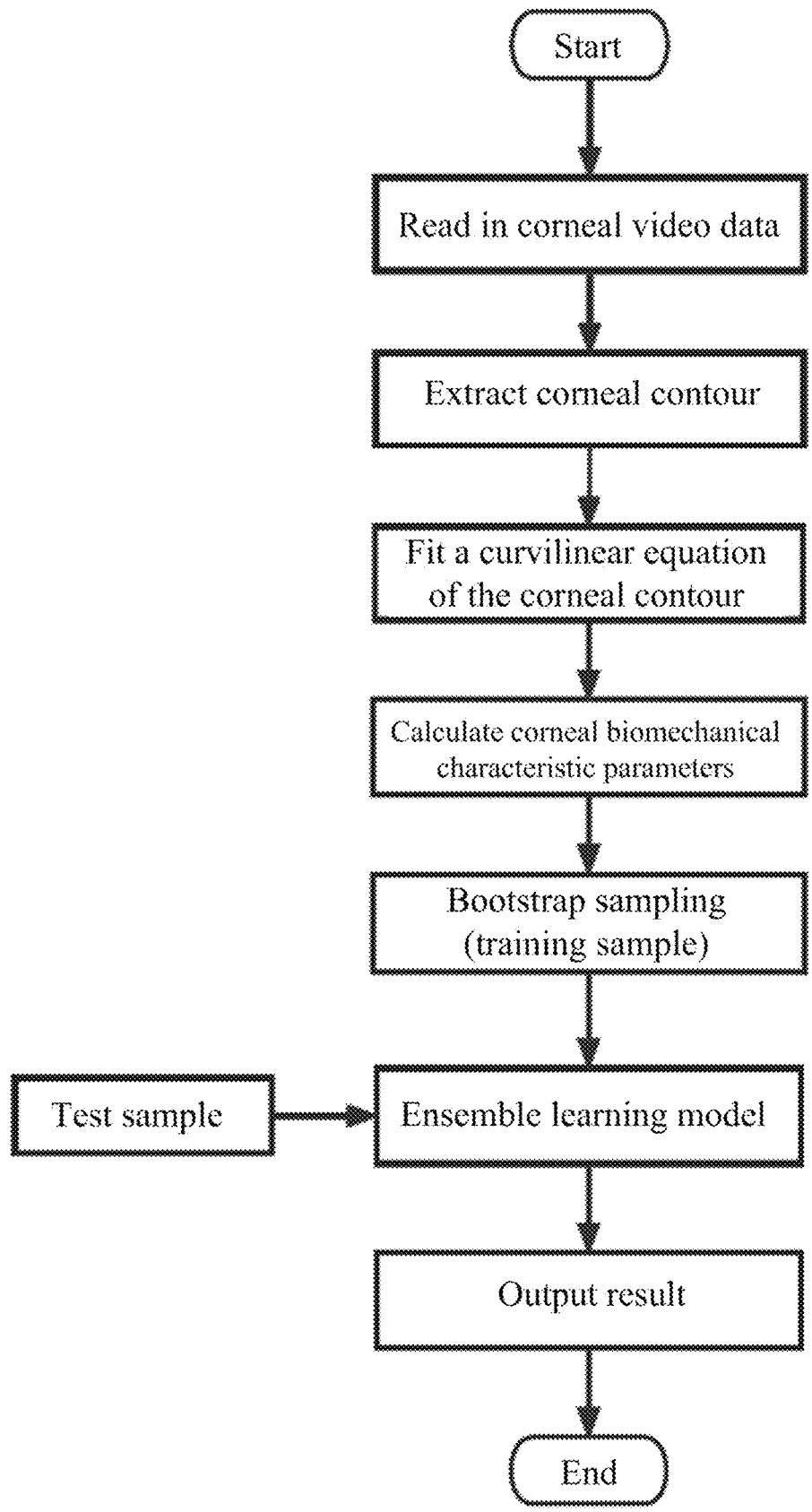
FIG. 1 is a flowchart of the present disclosure.

Embodiments of the present disclosure will be further described with reference to the accompanying drawings:

a subtle cornea deformation identification method based on a pixel-level corneal biomechanical parameter, as shown in FIG. 1, includes the following steps:

step 1: conduct sampling and analysis on a dynamic video of corneal stress deformation in a historical database, and calculate pixel-level data;

the step 1 is specifically as follows: acquire and partition the dynamic video of corneal stress deformation in a historical database, extract a corneal contour in each position according to a pixel, and fit a curvilinear equation of the corneal contour, and calculate the pixel-level data based on a pixel point.

The pixel-level corneal biomechanical parameter includes: variation of full contour length at first applanation, variation of full contour length at second applanation, maximum depression area, time at the first applanation, time at the second applanation, maximum curvature, depth of a thinnest point at the first applanation, depth of a thinnest point at the second applanation, depth of a thinnest point at maximum depression, length at the first applanation, length at the second applanation, peak distance, relative displacement of a thinnest point (1 mm), and relative displacement of a thinnest point (2 mm).

In the embodiment, the step 1 is specifically as follows: 31.88 ms video streaming data of the corneal stress deformation is sampled once every other 0.23 ms to obtain 139 images in total. Each image is subjected to contour extraction to obtain 576*200 corneal contour pixels, and a contour curvilinear equation is fitted, and 14 new pixel-level corneal biomechanical parameters are calculated based on a pixel point. The pixel-level corneal biomechanical parameter includes: variation of full contour length at first applanation, variation of full contour length at second applanation, maximum depression area, time at the first applanation, time at the second applanation, maximum curvature, depth of a thinnest point at the first applanation, depth of a thinnest point at the second applanation, depth of a thinnest point at maximum depression, length at the first applanation, length at the second applanation, peak distance, relative displacement of a thinnest point (1 mm), and relative displacement of a thinnest point (2 mm).

Step 2: configure an ensemble classifier according to a sampling result and detect a local change in corneal biomechanics, thus identifying a subtle cornea deformation.

Figure 2:
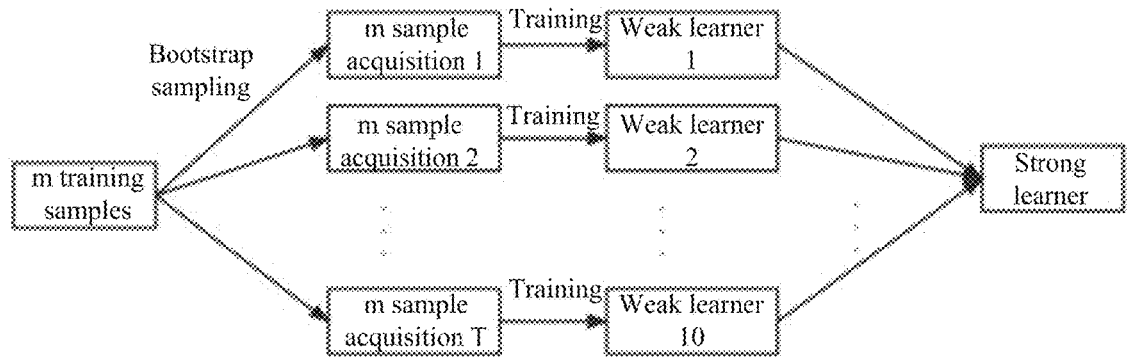
FIG. 2 shows a structure of Bagging (an ensemble classifier) according to the present disclosure.

As shown in FIG. 2, the step 2 is specifically as follows:

(1) configure a base classifier based on T sampling sets containing m training samples obtained by the sampling:

where a predicted label of x from an i-th base classifier is assumed as $h_i(x) \in \{-1, +1\}$ and the x has a real label of $y = f(x) \in \{-1, +1\}$ the base classifier has an error rate of $\epsilon$, namely, directed to each base classifier $h_i$, there exists:

$P(h_i(x) \neq f(x)) = \epsilon$

T base classifiers are combined by a voting method, and when more than half the base classifiers predict +1, ensemble classification gains +1, namely, when there are more than half base classifiers that predict 1, then $$\sum_{i=1}^{T} h_i(x) > 0$$

when there are more than half base classifiers that predict −1, then $$\sum_{i=1}^{T} h_i(x) < 0$$

and finally, the ensemble classifier has a result:

$$F(x) = \text{sgn}(H(x)) = \text{sgn}\left(\sum_{i=1}^{T} h_i(x)\right)$$

when the error rate of the base classifier is assumed independent, the ensemble classifier error rate is:

$$P(F(x) \neq f(x)) = \sum_{k=0}^{\lfloor T/2 \rfloor} \binom{T}{k}(1-\epsilon)^k \epsilon^{T-k}$$

that is, the error rate of the base classifier reduces exponentially as a number T of the base classifiers increases constantly; according to an inequation Hoeffding, when $\delta > 0, k = (p-\delta)n$;

$P(H(n) \leq (p-\delta)) \leq e^{-2\delta^2 n}$ when the ensemble classifier error rate is substituted into the inequation Hoeffding, and when $\delta > 0, k = (p-\delta)n \Rightarrow \lfloor T/2 \rfloor = (1-\epsilon-\delta)T$ $P(H(T) \leq (1-\Sigma-\delta)T) \leq e^{-2\delta^2 T}$ $\delta$ is settled according to a condition $\lfloor T/2 \rfloor = (1-\epsilon-\delta)T$ and substituted into the inequation above to solve an error rate of the ensemble classifier;

$$P(H(T) \leq \lfloor T/2 \rfloor) \leq e^{-2\delta^2 T} \leq e^{-2(1-\epsilon-\frac{1}{2})^2 T} = e^{-\frac{T}{2}(1-2\epsilon)^2}$$

(4) input the pixel-level corneal biomechanical parameter in the step 1 to each of the sampling sets, train a base learner, and integrate the base learners to obtain an ensemble learning model, and input a sample to be measured into the ensemble classifier, to obtain a sample category; and further, the sample category in the step (2) is obtained specifically by:

use a category with a maximum number of votes as the sample category by a voting method, and when two categories gain an equal number of votes, randomly choose one of the two categories as a final category of the sample.

Figure 3:
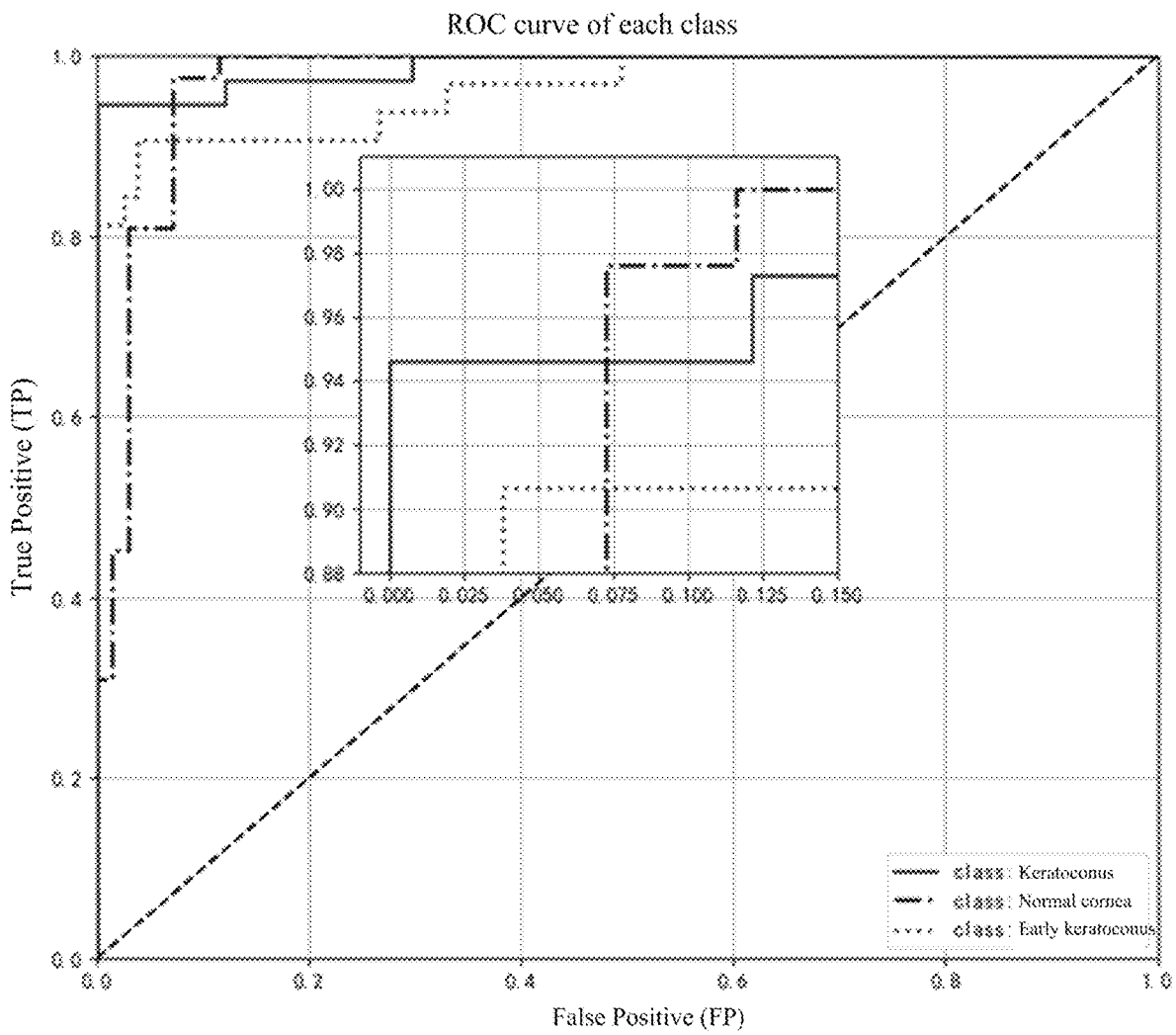
FIG. 3 shows a receiver operating characteristic (ROC) curve according to the present disclosure.

(5) calculate sample categories of all the samples to be measured, and determine a local change result of corneal biomechanics;

the determining a local change result of corneal biomechanics in the step (3) specifically includes:

(i) regarding one category and all other categories except for the one category as a dichotomous data model, as shown in FIG. 3, calculate a true positive rate (TPR) and a false positive rate (FPR), and define the FPR and the TPR as an x axis and a y axis, respectively, to obtain a visual receiver operating characteristic (ROC) curve;

where TPR denotes a capability to distinguish correctness from all positive samples and FPR denotes a capability to distinguish an error from all negative samples;

(ii) calculate a precision, a recall rate and an F1 Score to evaluate a performance of a tripartite model;

where the precision represents a proportion of correctly predicted quantities in predicted classification, and is equal to TP/(TP+FP);

the recall rate denotes a proportion of correctly predicted quantities in true classification, and is equal to TP/(TP+FN);

the F1 score denotes a harmonic mean of the precision and the recall rate; 1/F1 Score-½ (1/precision+1/recall rate);

where, T: predicted correct actually; F: predicted error actually; P: predicted positive; N: predicted negative; true positive (TP): determined as a positive accuracy; false positive (FP): false positive rate, namely, a negative is determined as a positive; and false negative (FN): false negative rate, namely, a positive is determined as a negative.

A subtle cornea deformation identification device based on a pixel-level corneal biomechanical parameter includes a pixel-level data computation module and a subtle cornea identification module;

the pixel-level data computation module is configured to conduct sampling and analysis on a dynamic video of corneal stress deformation in a historical database, and to calculate a pixel-level data; and the subtle cornea deformation identification module is configured to configure an ensemble classifier based on a sampling result, and detect a local change in corneal biomechanics, thus identifying subtle cornea deformation.

The pixel-level data computation module is configured to acquire and partition the dynamic video of corneal stress deformation in a historical database, extract a corneal contour in each position according to a pixel, and fit a curvilinear equation of the corneal contour, and calculate the pixel-level data based on a pixel point.

The pixel-level corneal biomechanical parameter includes: variation of full contour length at first applanation, variation of full contour length at second applanation, maximum depression area, time at the first applanation, time at the second applanation, maximum curvature, depth of a thinnest point at the first applanation, depth of a thinnest point at the second applanation, depth of a thinnest point at maximum depression, length at the first applanation, length at the second applanation, peak distance, relative displacement of a thinnest point (1 mm), and relative displacement of a thinnest point (2 mm).

In this embodiment, the above criterion is used to make statistics on the classification results of the sample to be measured (keratoconus KC: n=200; early keratoconus early KC: n=154, and normal cornea NC:n=200); and area under the curve (AUC): KC=0.989, early KC=0.963, and NC=0.973. The precision of the training set may be up to 100.00%; and the validation set has a precision of 93.00%, a recall rate of 92.79%, and an F1 Score of 92.83%.

TABLE 1

| | Classification result | | |
|---|---|---|---|
| | KC | early KC | NC |
| KC | 198 | 0 | 0 |
| early KC | 1 | 150 | 2 |
| NC | 1 | 4 | 198 |
| Total | 200 | 154 | 200 |

Those skilled in the art should understand that the embodiments of the present disclosure may be provided as a method, a system, or a computer program product. Therefore, the present disclosure may use a form of hardware only embodiments, software only embodiments, or embodiments with a combination of software and hardware. Moreover, the present disclosure may use a form of a computer program product that is implemented on one or more computer-usable storage media (including but not limited to a disk memory, a CD-ROM, an optical memory, and the like) that include computer-usable program codes.

The present disclosure is described with reference to the flowcharts and/or block diagrams of the method, the device (system), and the computer program product according to the embodiments of the present disclosure. It should be understood that computer program instructions may be used to implement each process and/or each block in the flowcharts and/or the block diagrams and a combination of a process and/or a block in the flowcharts and/or the block diagrams.

These computer program instructions may be provided for a general-purpose computer, a dedicated computer, an embedded processor, or a processor of another programmable data processing device to generate a machine, so that the instructions executed by a computer or a processor of another programmable data processing device generate an apparatus for implementing a specific function in one or more processes in the flowcharts and/or in one or more blocks in the block diagrams.

These computer program instructions may be stored in a computer-readable memory that can instruct the computer or any other programmable data processing device to work in a specific manner, so that the instructions stored in the computer-readable memory generate an artifact that includes an instruction apparatus. The instruction apparatus implements a specific function in one or more processes in the flowcharts and/or in one or more blocks in the block diagrams.

These computer program instructions may be loaded onto a computer or another programmable data processing device, so that a series of operations and steps are performed on the computer or another programmable device, thereby generating computer-implemented processing. Therefore, the instructions executed on the computer or another programmable device provide steps for implementing a specific function in one or more processes in the flowcharts and/or in one or more blocks in the block diagrams.

What is claimed is:

1. A subtle cornea deformation identification method based on a pixel-level corneal biomechanical parameter, comprising the following steps:

step 1, sampling and analyzing a dynamic video of corneal stress deformation in a historical database, and calculating pixel-level data; and step 2, configuring an ensemble classifier based on a sampling result and detecting a local change in corneal biomechanics, thus identifying a subtle cornea deformation, wherein sampling and analyzing the dynamic video of corneal stress deformation in the historical database, and calculating the pixel-level data further comprises: acquiring and partitioning the dynamic video of corneal stress deformation in the historical database, extracting a corneal contour in each position according to a pixel, fitting a curvilinear equation of the corneal contour, and calculating the pixel-level data based on a pixel point; and wherein the pixel-level data comprises all of: variation of full contour length at first applanation, variation of full contour length at second applanation, maximum depression area, time at the first applanation, time at the second applanation, maximum curvature, depth of a thinnest point at the first applanation, depth of a thinnest point at the second applanation, depth of a thinnest point at maximum depression, length at the first applanation, length at the second applanation, peak distance, relative displacement of a thinnest point (1 mm), and relative displacement of a thinnest point (2 mm).

2. The subtle cornea deformation identification method based on a pixel-level corneal biomechanical parameter according to claim 1, wherein configuring the ensemble classifier based on the sampling result and detecting the local change in corneal biomechanics, thus identifying the subtle cornea deformation further comprises:

(1) configuring a base classifier based on T sampling sets comprising m training samples obtained by the sampling as follows:

a predicted label of x from an i-th base classifier is assumed as $$h_i(x) \in \{-1, +1\}$$

and the x has a real label of $$y = f(x) \in \{-1, +1\}$$

the base classifier has an error rate of E, namely, directed to each base classifier $h_i$, there exists $$P(h_i(x) \neq f(x)) = \epsilon$$

T base classifiers are combined by a voting method, and when more than half of the base classifiers predict +1, ensemble classification gains +1, that is, when there are more than half base classifiers that predict 1, then $$\sum_{i=1}^{T} h_i(x) > 0$$

when there are more than half base classifiers that predict −1, then $$\sum_{i=1}^{T} h_i(x) < 0$$

and finally, the ensemble classifier has a result:

$$F(x) = \text{sgn}(H(x)) = \text{sgn}\left(\sum_{i=1}^{T} h_i(x)\right)$$

when the error rate of the base classifier is assumed independent, an ensemble classifier error rate is:

$$P(F(x) \neq f(x)) = \sum_{k=0}^{\lfloor T/2 \rfloor} \binom{T}{k}(1-\epsilon)^k \epsilon^{T-k}$$

that is, the error rate of the base classifier reduces exponentially as a number T of the base classifiers increases constantly; according to an inequation Hoeffding, when $$\delta > 0, k = (p-\delta)n;$$

$$P(H(n) \leq (p-\delta)) \leq e^{-2\delta^2 n}$$

when the ensemble classifier error rate is substituted into the inequation Hoeffding, and $$\delta > 0, k = (p-\delta)n \Rightarrow \lfloor T/2 \rfloor = (1-\epsilon-\delta)T$$

$$P(H(T) \leq (1-\epsilon-\delta)T) \leq e^{-2\delta^2 T}$$

$\delta$ is settled according to a condition $\lfloor T/2 \rfloor = (1-\epsilon-\delta)T$ and substituted into the inequation above to solve an error rate of the ensemble classifier;

$$P(H(T) \leq \lfloor T/2 \rfloor) \leq e^{-2\delta^2 T} \leq e^{-2\left(1-\epsilon-\frac{1}{2}\right)^2 T} = e^{-\frac{T}{2}(1-2\epsilon)^2}$$

(2) inputting the pixel-level corneal biomechanical parameter in the step 1 to each of the sampling sets, training a base learner, and integrating the base learners to obtain an ensemble learning model, and inputting a sample to be measured into the ensemble classifier, to obtain a sample class; and (3) calculating sample classes of all the samples to be measured, and determining a local change result of corneal biomechanics.

3. The subtle cornea deformation identification method based on a pixel-level corneal biomechanical parameter according to claim 2, wherein the sample category in the step (2) is obtained specifically by:

using a category with a maximum number of votes as the sample category by a voting method, and when two categories gain an equal number of votes, randomly choosing one of the two categories as a final category of the sample.

4. The subtle cornea deformation identification method based on a pixel-level corneal biomechanical parameter according to claim 3, wherein the determining a local change result of corneal biomechanics in the step (3) specifically comprises:

(i) regarding one category and all other categories except for the one category as a dichotomous data model to calculate a true positive rate (TPR) and a false positive rate (FPR), and defining the FPR and the TPR as an x axis and a y axis, respectively to obtain a visual receiver operating characteristic (ROC) curve;

wherein TPR denotes a capability to distinguish correctness from all positive samples, and FPR denotes a capability to distinguish an error from all negative samples;

(ii) calculating a precision, a recall rate and an F1 Score to evaluate a performance of a tripartite model;

wherein the precision represents a proportion of correctly predicted quantities in predicted classification, and is equal to TP/(TP+FP);

the recall rate denotes a proportion of correctly predicted quantities in true classification, and is equal to TP/(TP+FN);

the F1 score denotes a harmonic mean of the precision and the recall rate; 1/F1 Score=½ (1/precision+1/recall rate);

wherein, T: predicted correct actually; F: predicted mistaken actually; P: predicted positive; N: predicted negative; TP: determined as a positive accuracy; FP: false positive rate, namely, a negative is determined as a positive; and FN: false negative rate, namely, a positive is determined as a negative.

5. A subtle cornea deformation identification device based on a pixel-level corneal biomechanical parameter, comprising:

a pixel-level data computation module, configured to conduct sampling analysis on a dynamic video of corneal stress deformation in a historical database, and to calculate pixel-level data; and a subtle cornea deformation identification module, configured to configure an ensemble classifier based on a sampling result, and detect a local change in corneal biomechanics, thus identifying a subtle cornea deformation;

wherein the pixel-level data computation module is specifically configured to acquire and partition the dynamic video of corneal stress deformation in the historical database, extract a corneal contour in each position according to a pixel, fit a curvilinear equation of the corneal contour, and calculate the pixel-level data based on a pixel point; and the pixel-level data comprises all of: variation of full contour length at first applanation, variation of full contour length at second applanation, maximum depression area, time at the first applanation, time at the second applanation, maximum curvature, depth of a thinnest point at the first applanation, depth of a thinnest point at the second applanation, depth of a thinnest point at maximum depression, length at the first applanation, length at the second applanation, peak distance, relative displacement of a thinnest point (1 mm), and relative displacement of a thinnest point (2 mm).

* * * * *